United States Patent [19]

Bartl et al.

[11] 4,409,327
[45] Oct. 11, 1983

[54] PROCESS AND REAGENT FOR THE DETERMINATION OF THE BIOLOGICAL ACTIVITY OF HEPARIN IN PLASMA

[75] Inventors: Knut Bartl, Wilzhofen; Helmut Lill, Wielenbach; Peter Roeschlau, Seeshaupt; Joachim Ziegenhorn, Starnberg, all of Fed. Rep. of Germany

[73] Assignee: Boehringer Mannheim GmbH, Mannheim-Waldhof, Fed. Rep. of Germany

[21] Appl. No.: 233,536

[22] Filed: Feb. 11, 1981

[30] Foreign Application Priority Data

Feb. 14, 1980 [DE] Fed. Rep. of Germany ....... 3005540

[51] Int. Cl.³ .......................... C12Q 1/56; C12Q 1/38
[52] U.S. Cl. ...................................... 435/13; 435/23; 435/810
[58] Field of Search ...................... 435/23, 24, 13, 810

[56] References Cited

U.S. PATENT DOCUMENTS 4,191,808 3/1980 Nagatsu et al. ................... 435/24
4,234,682 11/1980 Bartl et al. .......................... 435/23
4,247,454 1/1981 Ekenstam et al. .................... 435/13

Primary Examiner—Esther M. Kepplinger
Attorney, Agent, or Firm—Felfe & Lynch

[57] ABSTRACT

Method and reagent for the determination of the biological activity of heparin in plasma by adding thrombin or Factor $X_a$ as the proteolytic enzyme and a chromogen substrate of the latter and measuring the dye liberated from the chromogen substrate in the absence of exogenous anti-thrombin III, the improvement consisting of adding, additionally, at least one compound of the formula

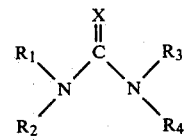

wherein
X is oxygen or the group $NR_5$;
and $R_1$, $R_2$, $R_3$, $R_4$ and $R_5$ are independently selected from hydrogen or alkyl of 1 to 2 carbon atoms.

10 Claims, 1 Drawing Figure

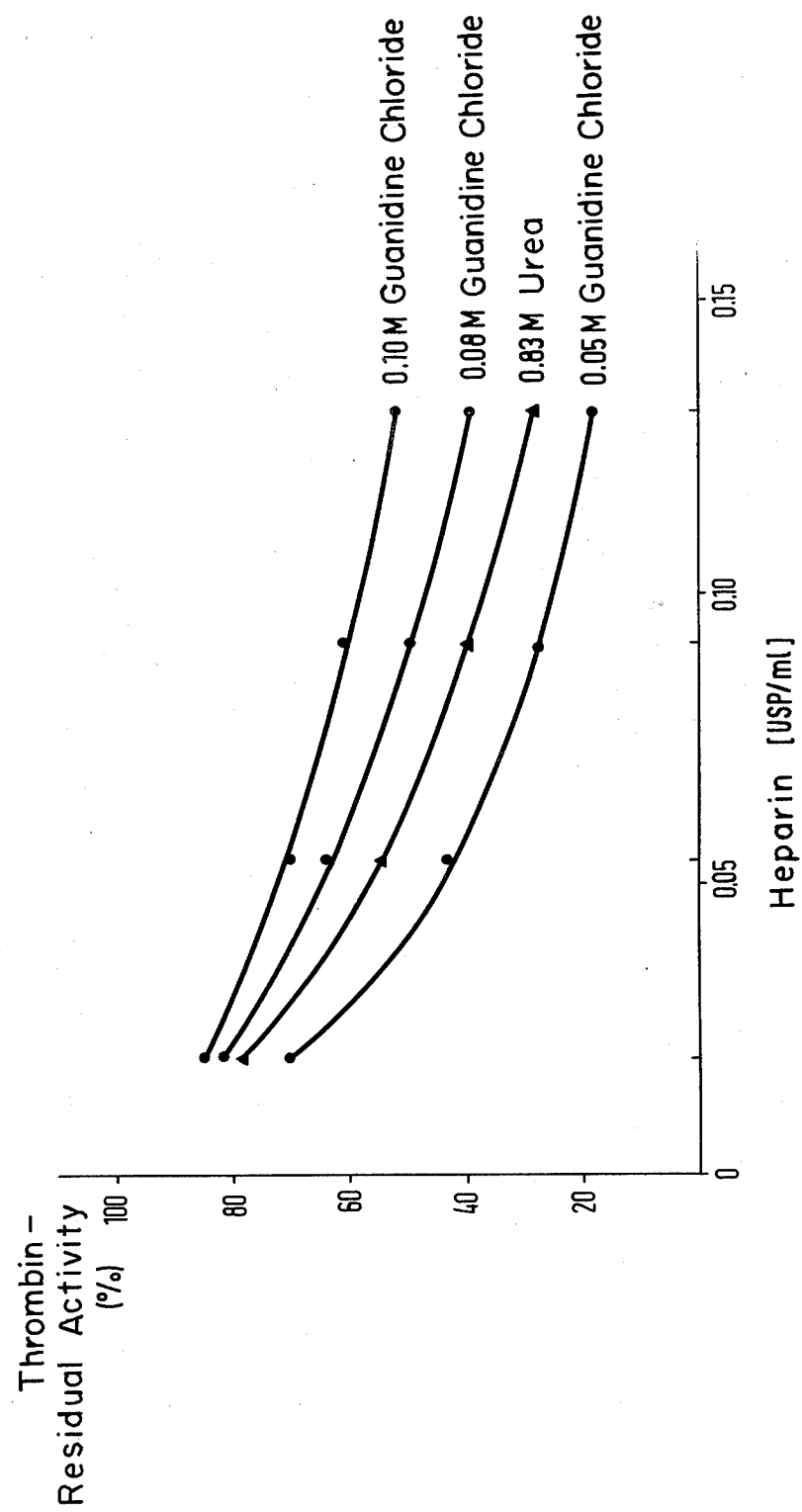

PROCESS AND REAGENT FOR THE DETERMINATION OF THE BIOLOGICAL ACTIVITY OF HEPARIN IN PLASMA

This invention relates to a method and a reagent for the determination of heparin in plasma.

Methods for the determination of the biological activity of heparin in plasma are conventional, as are methods which permit the determination of the amount of heparin, but not the actual activity thereof (see German Published Patent No. 28 12 943).

The conventional method of measuring heparin activity involves adding thrombin or Factor $X_a$ as a proteolytic enzyme and a chromogen substrate of the enzyme to plasma and measuring the dye liberated from the chromogen substrate, with the determination being carried out in the absence of exogenous antithrombin III.

This method increases the reliability of the heparin determination as an indicator and makes possible, in particular, the more meaningful use of the heparin concentration in heparin therapy where there is the danger of thrombosis. The method is especially suitable in normal heparin dosage (0.1 to 0.8 USP heparin/ml of normal plasma). At 37° C., however, even concentrations down to 0.02 USP/ml can be determined. In the lowest range, between 0.1 and 0.02, especially between 0.08 and 0.02 USP/ml of plasma, the accuracy of the determination, however, drops considerably, and under certain circumstances, values that vary considerably from the actual activities are found.

The present invention improves the conventional method in the lowest range of heparin activity, particularly in increasing its sensitivity and reliability sufficiently to avoid stray results, and improving the accuracy of the determination in this range to diagnostically acceptable error ranges.

Surprisingly, it was now found that this aim can be realized by adding urea and certain urea derivatives to the reaction mixture.

The method according to the present invention for determining the biological activity of heparin in plasma by adding thrombin or factor Xa as the proteolytic enzyme and a chromogen substrate of the enzyme and measuring the dye liberated from the chromogen substrate, with the determination being carried out in the absence of exogenous antithrombin III, is characterized in that, in addition, at least one compound of the general formula

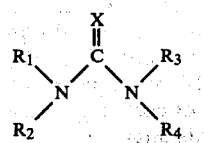

is added, in which X represents an oxygen atom or the group $NR_5$, and $R_1$, $R_2$, $R_3$, $R_4$, and $R_5$, independent of each other in each case, represent an H atom or an alkyl group with 1 to 2 C atoms.

It is preferable that the amount added be 0.02 to 2.0 mol/l, referred to the reaction mixture. Addition of between 0.2 and 1.0 mol/l is especially preferred if X is an oxygen atom, and of 0.05 to 0.2 mol/l, if X is the group $NR_5$.

With the method according to the present invention, it is possible, even at 25° C., to still determine heparin activity down to about 0.02 USP/ml with great sensitivity and accuracy. Thus, the method according to the present invention is especially suited for so-called low-dose therapy for prophylaxis for thrombosis complications, where 0.02 to 0.1 USP heparin/ml is administered. Until now a really practicable method that can also be automated has not been available for this therapeutic method, which is carried out in the lowest range. In J. Clin. Chem. Clin. Biochem. 17 (1979): 184/85, to be sure, a method for the determination of heparin in the low range indicated has already been described. This has two substantial disadvantages, however. For one thing, in a differential measurement, only the effect of the heparin used is detected. According to the method of the present invention, on the other hand, the total anticoagulant effect of the plasma is detected; thus, the decisive parameter for the physician in practice. Besides, because of the necessity of a differential measurement, a second measuring step is required, in which platelet factor IV is added as a heparin neutralizing agent. This impedes the possibility of automating the known method and, at the same time, too, its use in the clinical routine.

In other respects, the statements made in German Published Patent No. 28 12 943 are accordingly valid, with the exception of the increased use of the sample, for carrying out the method of the present invention. It is, thus, preferable to use as the chromogen substrate a peptide that exhibits a p-nitroanilido radical bound by an amido bond to the carboxyl group of an arginine radical. If thrombin is used, Bz-Phe-Val-Arg-pNA, H-D-Phe-Pip-Arg-pNA, or Tos-Gly-Pro-Arg-pNA proved to be especially suitable as substrates. If enzyme factor $X_a$ is used, Bz-Ile-Glu-Gly-Arg-pNA has proved to be good as the chromogen substrate. It is convenient, moreover, to add to the reagent aprotinin and EDTA, as well as alkali chloride and a buffer, pH 6 to 9, and if necessary, polyethylene glycol, too. A pH-value of about 8 is preferred, as well as tris buffer (tris-(hydroxymethyl)-aminomethane/HCl). Other examples of suitable buffers are tris/imidazole or imidazole/HCl buffer.

The method can be carried out both kinetically and according to the end-value method. The evaluation can conveniently be done against a calibration curve.

Additional subject matter of the invention is a reagent for carrying out the method according to the present invention, containing 0.01 to 0.2 mol/l of buffer, pH 6 to 9,
0.05 to 0.25 mol/l of alkali chloride,
200 to 1100 NIH/l of thrombin or factor $X_a$,
0.12 to 12 mmol/l of chromogen substrate,
0 to 0.01 g/l of aprotinin,
0 to 0.03 mol/l of EDTA, and
0 to 10 g/l of polyethylene glycol, which is characterized by a content of at least 0.02 to 2.0 mol/l of a compound of the general formula

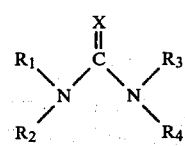

in which X represents an oxygen atom or the group $NR_5$, and $R_1$, $R_2$, $R_3$, $R_4$, and $R_5$, independently of each other in each case, represent an H atom or an alkyl group with 1 to 2 C atoms.

The reagent according to the present invention is quite stable in the dry state. After preparing a solution of the reagent for use by adding water, the stability lasts about a week.

The FIGURE in the attached drawing shows the increase in sensitivity achieved for guanidine hydrochloride and urea as a function of the quantity added. A standard on a plasma base (0.1 ml) was used as the sample.

The following examples further explain the present invention.

EXAMPLE 1

The activity of 0.08 USP heparin/ml of normal plasma was determined, expressed as the percentage of radical activity, with urea being added in one series of tests, and this addition not being made in another series of tests.

2.0 ml of a reagent mixture of the following composition:
0.2 mol/l of tris/HCl, pH 7.5,
0.07 mol/l of NaCl,
330 NIH/l of thrombin,
0.01 g/l of aprotinin,
0.01 mol/l of EDTA, and
10 g/l of polyethylene glycol
were mixed with 0.050 ml of the sample to be investigated and incubated at 25° C. for 180 seconds. Then 0.20 ml of a 1.5 mmol/l solution of Tos-Gly-Pro-Arg-pNA was added, and the extinction change per minute was determined for 2 minutes.

In another experiment, the sample was replaced by an equal quantity of distilled water. The value thus obtained was used as a basis for starting value=100%.

The determination was carried out in five parallel tests. The results are indicated in Table 1.

The tests were repeated in the same way, but in so doing, 50 g of urea (0.83 mol/l) was added to the reaction mixture, according to the present invention. The results of these tests are also shown in Table 1.

TABLE 1

| Thrombin Activity in Percent | |
|---|---|
| Reagent without urea | Reagent with urea (according to the present invention) |
| 79.9 | 61.5 |
| 61.5 | 60.6 |
| 79.5 | 60.2 |
| 79.5 | 58.8 |
| 64.6 | 58.8 |

The test results in Table 1 show that in carrying out the method of determination without the addition of urea, uncertain and, to some extent, very wrong results appear. With the addition of urea, according to the present invention, results that can be reproduced very well are obtained.

EXAMPLES 2 TO 6

The procedure as described in Example 1 was used, with the difference that instead of urea, the urea derivatives of the general formula indicated in Table 2 were used in the quantities also indicated in the table. The results corresponded to those of Example 1.

TABLE 2

| Example | Compound of the general formula | Quantity added (mol/l) |
|---|---|---|
| 2 | Guanidine hydrochloride | 0.08 |
| 3 | N—methyl urea | 0.8 |
| 4 | N,N—dimethylurea | 0.4 |
| 5 | N,N'—dimethylurea | 0.8 |
| 6 | Tetramethylurea | 0.2 |

It will be understood that the specification and examples are illustrative, but not limitative of the present invention and that other embodiments within the spirit and scope of the invention will suggest themselves to those skilled in the art.

What is claimed is:

1. In a method for the determination of the biological activity of heparin in plasma by adding thrombin or factor $X_a$ as a proteolytic enzyme and a chromogen substrate of the latter, and measuring the dye liberated from the chromogen substrate, wherein the determination is carried out in the absence of exogenic anti-thrombin III, the improvement consisting of adding to the reaction mixture 0.02 to 2.0 mole per liter based on the total reaction mixture of at least one compound of the formula

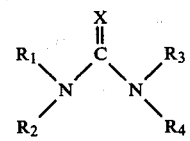

wherein
X is oxygen or the group $NR_5$; and
$R_1$, $R_2$, $R_3$, $R_4$ and $R_5$ are independently selected from hydrogen or alkyl of 1 to 2 carbon atoms, so that the proteolytic enzyme acts in the presence of said compound.

2. The improvement as claimed in claim 1 wherein X in the formula is oxygen.

3. The improvement as claimed in claim 2 wherein 0.2 to 1.0 mole of said compound are added per liter of reaction mixture.

4. The improvement as claimed in claim 1 wherein X in the formula is $NR_5$.

5. The improvement as claimed in claim 4 wherein 0.05 to 0.2 mole of said compound are added per liter of reaction mixture.

6. Reagent for the determination of the biological activity of heparin in plasma comprising
0.01 to 0.2 mol/l of buffer, pH 6 to 9;
0.05 to 0.25 mol/l alkali chloride;
200 to 1100 NIH/l of thrombin or factor Xa;
0.12 to 12 mol/l of chromogen substrate;
0 to 0.01 g/l of aprotinin;
0 to 0.03 mol/l EDTA;
0 to 10 g/l of polyethylene glycol; and
0.02 to 2.0 mol/l of a compound of the formula

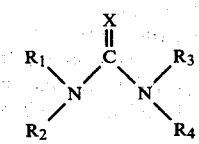

wherein

X is oxygen or the group $NR_5$; and $R_1$, $R_2$, $R_3$, $R_4$ and $R_5$ are independently selected from hydrogen or alkyl of 1 to 2 carbon atoms.

7. Reagent as claimed in claim 6 wherein X in the formula is 0.

8. Reagent as claimed in claim 7 wherein 0.02 to 2.0 mole per liter of said compound is added, based on the total reaction mixture.

9. Reagent as claimed in claim 6 wherein X in the formula is $NR_5$.

10. Reagent as claimed in claim 9 wherein 0.05 to 0.2 mole of said compound are added per liter of reaction mixture.

* * * * *